United States Patent
Soomro et al.

(10) Patent No.: US 9,554,706 B2
(45) Date of Patent: Jan. 31, 2017

(54) SYSTEM AND METHOD FOR HIGHLY RELIABLE DELIVERY OF LIFE-CRITICAL ALARMS THROUGH SHARED WIRELESS CHANNELS

(75) Inventors: Amjad A. Soomro, Hopewell Junction, NY (US); Mark S. Kotfila, Chelmsford, MA (US); Ruediger Schmitt, Maplewood, NJ (US); Phillip Raymond, Windham, NH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 534 days.

(21) Appl. No.: 13/636,039

(22) PCT Filed: Mar. 9, 2011

(86) PCT No.: PCT/IB2011/050990
§ 371 (c)(1),
(2), (4) Date: Sep. 19, 2012

(87) PCT Pub. No.: WO2011/124993
PCT Pub. Date: Oct. 13, 2011

(65) Prior Publication Data
US 2013/0015966 A1 Jan. 17, 2013

Related U.S. Application Data

(60) Provisional application No. 61/321,166, filed on Apr. 6, 2010.

(51) Int. Cl.
G08B 23/00 (2006.01)
A61B 5/00 (2006.01)
G08B 25/00 (2006.01)

(52) U.S. Cl.
CPC ............ *A61B 5/002* (2013.01); *A61B 5/0006* (2013.01); *A61B 5/0031* (2013.01); *G08B 25/004* (2013.01)

(58) Field of Classification Search
CPC ..... A61B 5/002; A61B 5/0022; A61B 5/0002; A61B 5/0004; A61B 5/02; A61B 5/0006; A61B 5/746; A61B 5/0205; A61B 5/02055; A61B 5/0015; A61B 2560/0271; A61B 5/0836; G08B 25/004; G08B 23/00; G08B 25/002; G08B 21/0453; G06F 19/327; G06F 19/322; G06F 19/30; G06F 19/3418; H04L 45/22; H04L 45/70; H04L 67/12; H04W 40/12; H04W 4/023; H04W 72/10; H04W 84/12; Y10S 128/903; Y10S 128/00; A61M 2205/3553; A61M 2205/3561; A61M 2205/3592
(Continued)

(56) References Cited

U.S. PATENT DOCUMENTS 6,659,947 B1 12/2003 Carter et al.
7,515,043 B2 4/2009 Welch et al.
(Continued)

FOREIGN PATENT DOCUMENTS

CN 2731606 Y 10/2005
CN 101524271 A 9/2009
(Continued)

OTHER PUBLICATIONS

Rosenberg, et al. "Standards Track" RFC3261—SIP: Session Initiation Protocol Copyright 2002 The Internet Society pp. 1-269.
(Continued)

*Primary Examiner* — Mirza Alam

(57) ABSTRACT

A patient monitor includes a plurality of monitoring devices which collect data about a patient. An evaluation unit determines the patient's condition from the collected data and generates an alarm if the patient's condition warrants notifying an appropriate medical responder. A communica-
(Continued)

Figure 1:
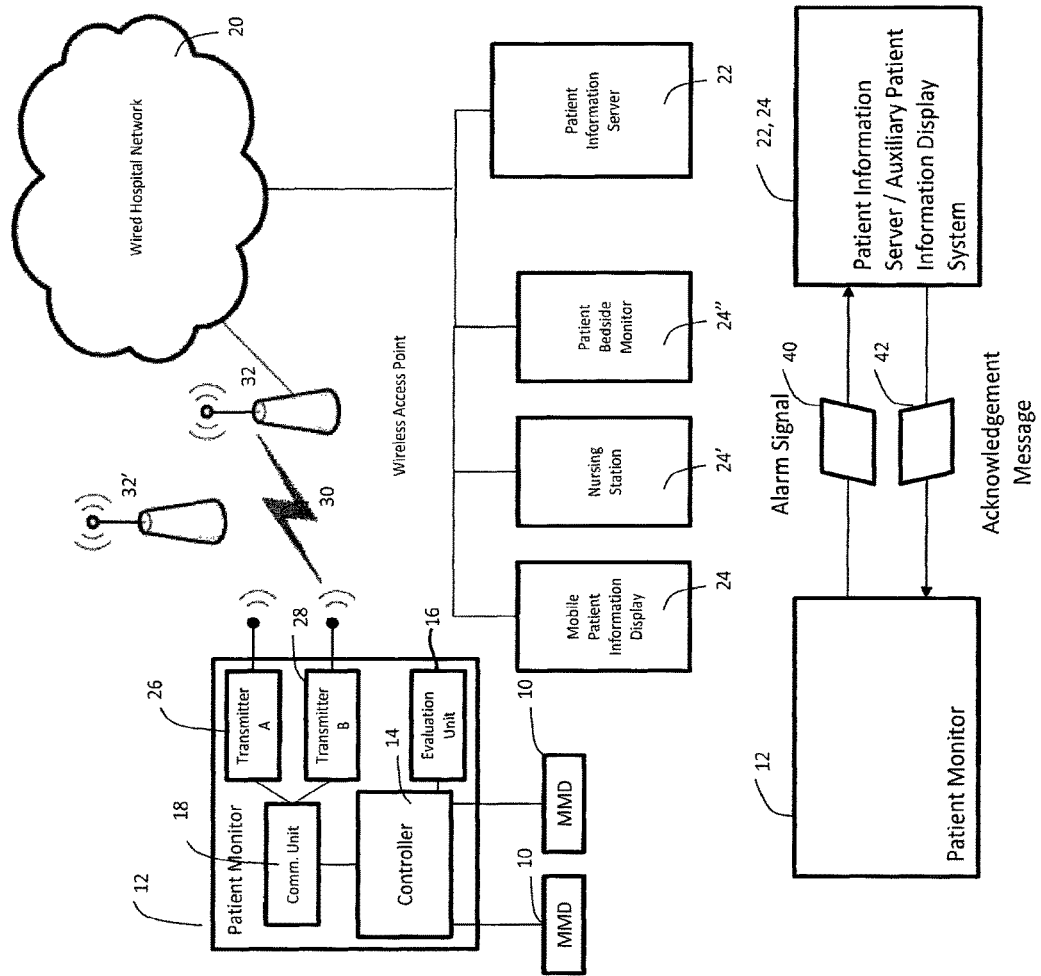

tion unit which transmits the alarm to a access point over a hospital Internet protocol (IP) network, the communication device includes a first transmitter for transmitting the alarm using a primary link and a second transmitter for transmitting the alarm using a secondary link in response to the transmission using the primary link failing.

8 Claims, 3 Drawing Sheets

(58) Field of Classification Search
USPC .............................. 340/502, 573.1, 539.12, 870.01–870.03,340/426.18, 539.13, 539.11; 600/300, 301, 509, 600/515; 370/338, 235, 241, 310, 328, 389; 128/920, 903, 925, 904
See application file for complete search history.

(56) References Cited

U.S. PATENT DOCUMENTS

| | | | |
|---|---|---|---|
| 8,791,815 | B2 | 7/2014 | Mazar et al. |
| 2003/0023146 | A1* | 1/2003 | Shusterman ....... A61B 5/02055 600/300 |
| 2003/0206535 | A1 | 11/2003 | Shpak |
| 2004/0010616 | A1 | 1/2004 | McCanne |
| 2004/0170154 | A1* | 9/2004 | Carter ................. A61B 5/0006 370/338 |
| 2005/0148890 | A1 | 7/2005 | Hastings |
| 2006/0001551 | A1 | 1/2006 | Kraft et al. |
| 2006/0094936 | A1 | 5/2006 | Russ |
| 2007/0076655 | A1 | 4/2007 | Manjeshwar et al. |
| 2007/0213600 | A1* | 9/2007 | John .................. A61B 5/0031 600/300 |
| 2008/0194925 | A1 | 8/2008 | Alsafadi et al. |
| 2008/0219281 | A1 | 9/2008 | Akin et al. |
| 2008/0285462 | A1* | 11/2008 | Baker ................. H04W 16/18 370/241 |
| 2009/0086759 | A1 | 4/2009 | Heise et al. |
| 2009/0274149 | A1 | 11/2009 | Williams et al. |
| 2012/0229271 | A1* | 9/2012 | Davis ................... G08B 25/004 340/539.12 |

FOREIGN PATENT DOCUMENTS

| | | |
|---|---|---|
| EP | 1892917 B1 | 2/2009 |
| WO | 2007047128 A1 | 4/2007 |
| WO | 2008036518 A1 | 3/2008 |

OTHER PUBLICATIONS

Wedlund, "Mobility Support Using SIP", Second ACM/IEEE Int'l Conf. on Wireless and Mobile Multimedia, Copyright ACM 1999 pp. 76-82.
Schulzrinne, et al. "Application-Layer Mobility Using SIP" Mobile Computing and Communications Review, V. 4, No. 3, pp. 47-57.
Boysen, et al. "Proactive Handover Using SIP", Unclassified/Unlimited RTO-MP-INS-083 pp. 17-1-17-10.
Bamerjee, et al. "Seamless SIP-Based Mobility for Multimedia Applications", IEEE Network Mar./Apr. 2006, pp. 6-13.
Yuce, et al., "A Wireless Medical Monitoring Over a Heterogeneous Sensor Network", Proceedings of 29th Annual Int'l Conference of IEEE EMBS, Lyon France, Aug. 23-26, 2007 pp. 5894-5898.
Belghoul, et al., "IP-Based Handover Management Over Heterogeneous Wireless Networks", Proceedings of 28th Annual EIII Int'l Conference on Local Computer Networks (LCN'03) 2pp.
Kawaguchi, et al., "Nat Free Open Source 3D Video Conferencing Using SAMTK and Application Layer Router", 978-14244-2309-5/09/$25.00 (c) 2009 IEEE, 2pp.
Niyato, et al., "Remote Patient Monitoring Service Using Heterogeneous Wireless Access Networks: Architecture and Optimization", IEEE Journal on Selected Areas in Communications, V. 27, N. 4, May 2009, pp. 412-423.
Mies, et al., "Towards End-To-End Connectivity for Overlays Across Heterogeneous Networks", 978-1-4244-3437-4/09/$25.00 (c) 2009 IEEE, 6pp.
Tinnirello, I., et al.; Interference Estimation in IEEE 802.11 Networks; 2010; IEEE Control Systems Magazine; 30 (2)30-43.

* cited by examiner

SYSTEM AND METHOD FOR HIGHLY RELIABLE DELIVERY OF LIFE-CRITICAL ALARMS THROUGH SHARED WIRELESS CHANNELS

CROSS REFERENCE TO RELATED APPLICATIONS

This application claims the benefit of U.S. provisional application Ser. No. 61/321,166 filed Apr. 6, 2010, which is incorporated herein by reference.

The following relates to the medical arts, communication arts, and related arts. It finds particular application in improving the communication in medical monitoring systems, medical alarm systems, and the like, through underlying networks in hospitals, urgent care centers, homes, nursing homes, assisted care facilities, emergency medical transportation vehicles and systems, and the like.

Presently, patient monitoring systems continuously monitor a patient's physiological condition, for example, in an intensive care unit (ICU). The physiological data collected from the patient is analyzed, for example, in a bedside monitor or a patient information server. The analysis indicates whether the patient's condition warrants notifying an appropriate medical responder by generating alarms. When alarms are generated by medical devices they need to traverse communication channels to be delivered to the appropriate medical responder.

In life-critical medical data applications, such as real-time ambulatory patient monitoring over wireless links, patients often wear battery-powered or mobile monitoring devices, such as heart patients wearing a mobile ECG device. It is a requirement that alarms generated by a monitoring device are communicated to medical responder in timely manner, typically specified by regulatory authorities. However, it is desirable to use existing wireless infrastructure in healthcare facilities, such as a IEEE 802.11 network, to carry medical data including data for life-critical medical applications. However, wireless channels are inherently error prone from noise, network congestion, and the like.

The present application provides a new and improved patient monitoring system and method which overcomes the above-referenced problems and others.

In accordance with one aspect, a method for transmitting an alarm is provided. A communication link between a multi-mode patient monitoring device and an access point over a network is established, by which the patient monitoring device communicates using a hospital Internet protocol network via the access point. Physiological data collected from by the patient monitoring device is processed to determine whether a patient's condition warrants generating an alarm. The alarm is transmitted using a primary channel between the patient monitor and the access point. The alarm is transmitted using a secondary channel between the patient monitor and the access point in response to attempts to transmit the alarm using the primary channel failing.

In accordance with another aspect, a patient monitor is provided. A plurality of monitoring devices collect data about a patient. An evaluation unit determines the patient's condition from the collected data and generates an alarm if the patient's condition warrants notifying an appropriate medical responder. A communication unit which transmits the alarm to a access point over a hospital Internet protocol (IP) network, the communication device includes a first transmitter for transmitting the alarm using a primary channel and a second transmitter for transmitting the alarm using a secondary channel in response to the transmission using the primary channel failing.

One advantage is the consistent delivery of medical alarms to an appropriate medical responder using existing wireless infrastructure.

Another advantage resides in power savings for the patient monitoring device.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

FIG. 1 is a diagrammatic illustration of a patient monitoring system in accordance with the present application.

Figure 2:
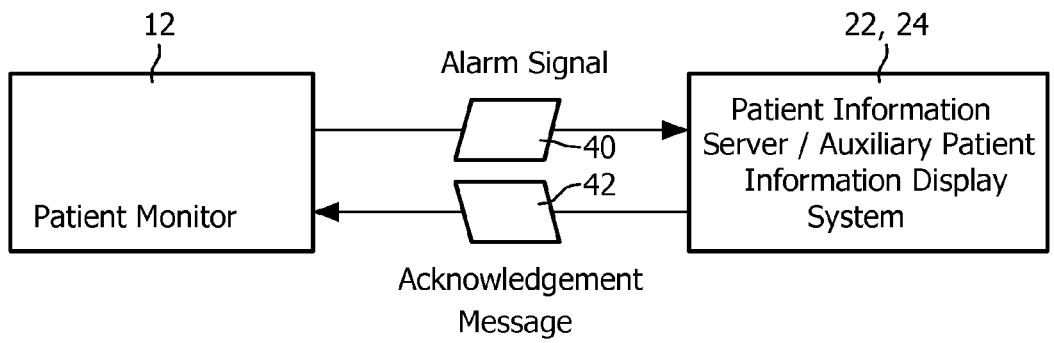

FIG. 2 diagrammatic illustration of a patient monitoring device/patient information server relationship.

Figure 3:
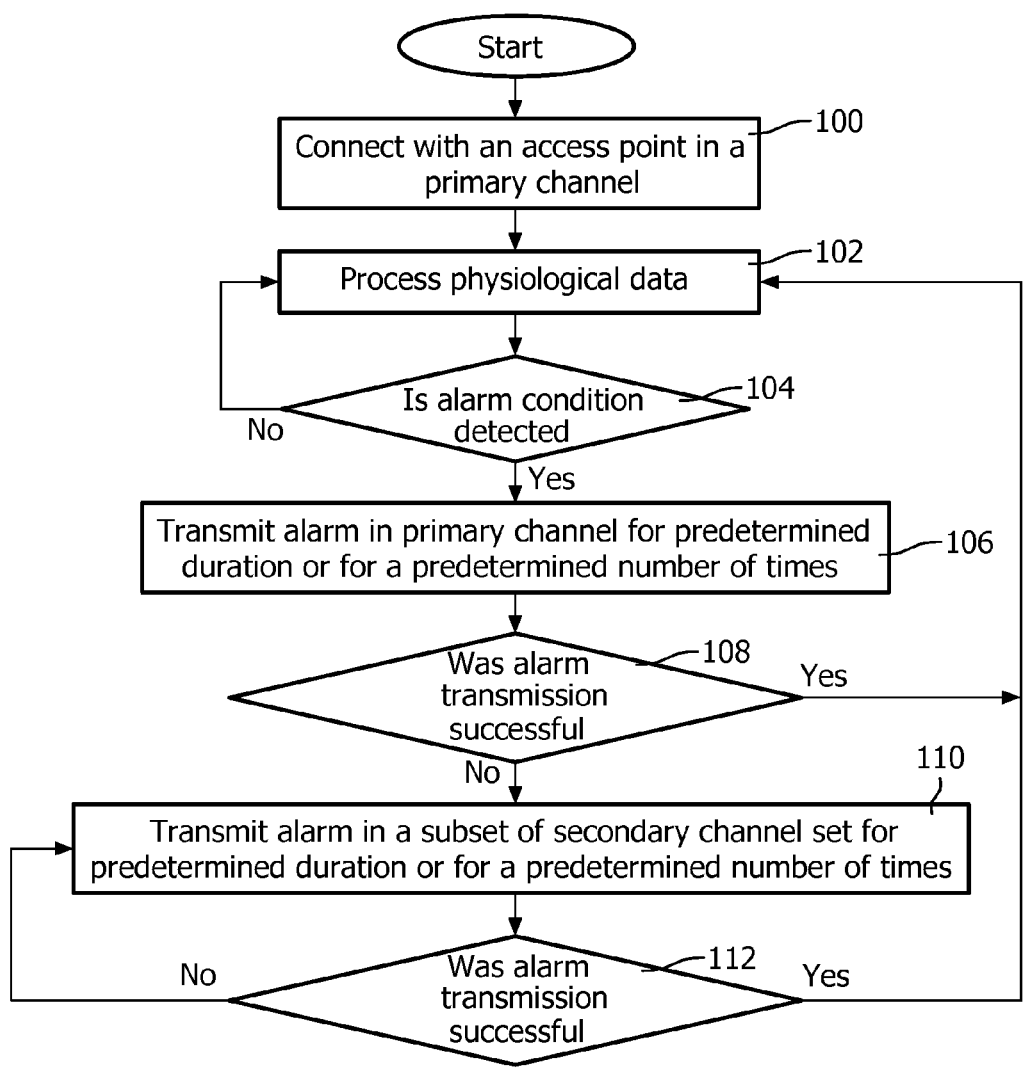
Figure 4:
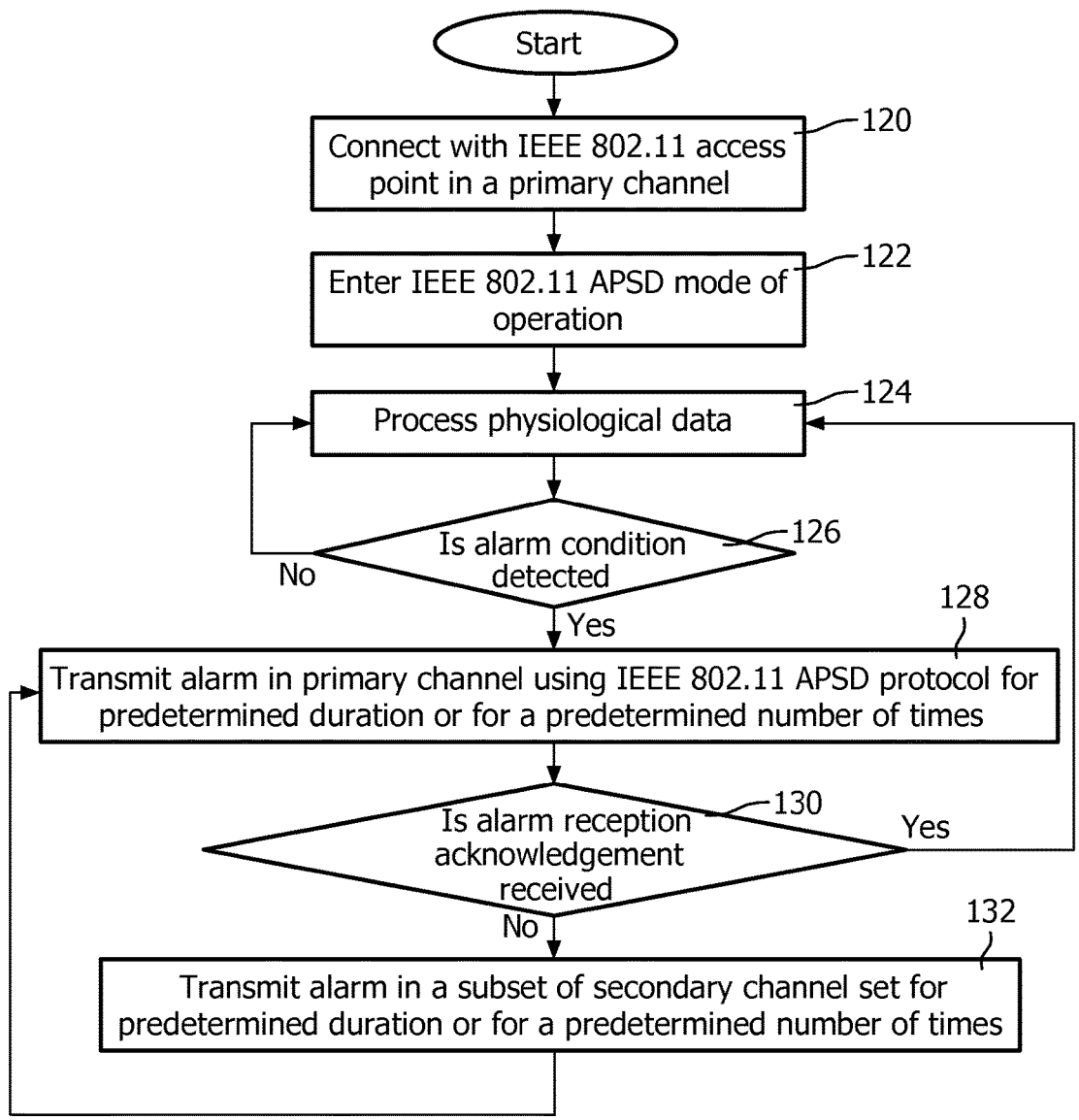

FIGS. 3 and 4 are flowchart diagrams of the operation of the patient monitoring device in accordance with the present application.

With reference to FIG. 1, a patient (not shown) is monitored by various medical monitoring devices or sensors 10 that measure physiological parameters of the patient and generate physiological data indicative thereof. These medical monitoring devices 10 may include an electrocardiographic (ECG) instrument with ECG electrodes, and a wrist-based medical monitor, which may for example be configured to monitor blood pressure, blood oxygenation ($SpO_2$), pulse, or one or more other physiological parameters. Other medical monitoring devices 10 can be associated with a patient, and not all of the above-mentioned medical monitoring devices 10 have to be associated with a patient at any given time. It should be appreciated that while only two medical monitoring devices 10 are illustrated, more medical monitoring devices are contemplated. As used herein, medical monitoring devices signifies data sources indicating patient health, or the like. Electronics for receiving signals from the medical monitoring device and for optionally performing signal processing on such signals are embodied in the illustrated embodiment as a multi-functional patient monitor device (PMD) 12, or may be embodied partly or wholly as on-board electronics disposed with one or more of the medical monitoring devices 10 or so forth. It should also be appreciated that the medical monitoring devices 10 and the PMD 12 could also be embodied into a single device. The PMD 12, for example, may be a monitor that travels with the patient, such as the transmitter of an ambulatory patient worn monitoring system, or the like.

The medical monitoring devices 10 report the measured or other physiological data to the PMD 12. The PMD 12 serves as a gathering point for the physiological data measured by the medical monitoring devices, and provides temporary storage for the data. The collected physiological data is concurrently transmitted to a controller 14 in the PMD 12. A physiological evaluation unit 16 or computer program in the PMD evaluates the physiological data collected from the patient and determines whether the patient's condition warrants notifying an appropriate medical responder by generating an alarm signal. For example, the PMD 12 checks whether each measured parameter is approaching threshold values, whether a trend of any parameter is approaching a threshold, whether any parameter lacks stability or fluxuates too much, combinations of parameters are approaching a threshold, and other indicators that a patient needs more or less medical monitoring or assistance. The thresholds include values exceeding or falling below a limit based on time, severity, escalation, or the like.

The PMD 12 also includes a communication unit 18 for transmitting the alarm signal wirelessly through a hospital network 20 to a patient information server 22 where the patient's alarms are displayed and stored. The patient's alarm signals can also be transmitted through the hospital network 20 to mobile patient information display systems 24. For example, a nurse may view or hear a patient's alarms at a nursing station 24', on the patient's bedside monitor 24", another patient's bedside monitor, a central monitoring station, a PDA, or the like. It should be appreciated that while only three mobile patient information displays 24 are illustrated, more mobile patient information displays are contemplated. The communication unit 18 controls a first transmitter 26 and a second transmitter 28 to transmit the physiological data, received by the controller 14, and receive acknowledgements of received data, on primary and secondary channels to the hospital network 20. The first transmitter 26 initially attempts to transmit the alarm signal to the hospital network 20 using a primary channel. The primary channel is a channel which is pre-programmed to be used when the patient monitoring system is operating normally. For example, a primary channel could be a shared wireless channel using IEEE 802.11 or Wi-Fi network technologies. A primary channel could also be selected from a list of available wireless channels using IEEE 802.11 or Wi-Fi network. The primary channel could be a specific band of radio frequency or a communication protocol. The selection of a primary channel could be performed by user configuration or it could be done dynamically in a system, for example, by running channel selection algorithms either at the PMD or by other entities of the system, for example, by the infrastructure access points or by wireless channel management functions.

Should the attempt(s) to transmit the alarm signal in primary channel fail with the first transmitter 26, the communication unit 18 controls the second transmitted 28 to transmit the alarm signal on secondary channels concurrently with the first transmitter 26 to maximize the probability of delivery of the alarm signal. The transmissions in the secondary channel are preferably transmitted in a broadcast mode. Alternately, the transmissions in the secondary channel are sent unicast to a pre-determined list of receivers in the secondary channel(s). Preferably, the transmissions in secondary channel(s) would occur after transmission(s) in primary channel are not successful and substantially immediate after such determination, without performing the association protocols of wireless network of the secondary channel. The secondary channel(s) are proposed to be one or more of the following: a specific band of radio frequency, a communication protocol, or more specifically, one or more channels used for asset tracking tags, communication protocol(s) used for asset tracking tags in IEEE 802.11 networks, one or more channels used for RFID tags, one or more channels used for IEEE 802.15.4 radios, one or more channels used for Zigbee radios, one or more channel used for Bluetooth radios, one or more predetermined duration(s) and location(s) within a beacon time period of an IEEE 802.11 network, one or more time periods within beacon time period which are expected to have high probability of availability, such as time periods immediately before target beacon transmission times (TBTT) of IEEE 802.11 network, one or more dedicated IEEE 802.11 wireless channels reserved for transmissions should attempts to transmit in primary channel fail, one or more channels used for cellular networking technologies, such as, IP Multimedia Subsystem (IMS), GPRS, UMTS, CDMA2000, IS-95, GSM, CDMA, CDMA 1×, CDMA 1× EV-DO, UMTS over W-CDMA, UMTS over TDD, CDMA 3× EV-DO, HSPA D, HSPA U, EDGE, one or more channels used for broadband wireless access such as, IEEE 802.16, WiMAX, IEEE 802.22, or the like.

The alarm signal is communicated to the hospital network 20 via a wireless communication link 30 between the PMD 12 and a wireless access point (WAP) 32. The communication link 30 employs an IEEE 802.11 protocol including quality of service (QoS) extensions, denoted generically herein as an 802.11-QoS protocol. In some embodiments, the 802.11-QoS protocol conforms with the IEEE 802.11e standard. In some embodiments, the 802.11-QoS protocol conforms with the IEEE 802.11 EDCA standard, where the acronym "EDCA" represents "enhanced distributed channel access." The 802.11-QoS protocol may also employ a subset of the standard IEEE 802.11e protocol (i.e., some features not implemented), or may employ a superset of the standard IEEE 802.11e protocol (additional features added), or may employ a modified protocol based on IEEE 802.11e but with some features added to the standard and some standard features not implemented. It will be appreciated that the communication links 30 are illustrative examples, and that typically the communication system complying with the 802.11-QoS protocol may support several, several dozen, or more such communication links. Similarly, while the single WAP 32 is illustrated, typically the communication system complying with the 802.11-QoS protocol may include one, two, three, four, ten, twenty, or more wireless access points distributed through the hospital or other medical setting to provide desired coverage area for the communication system. Additionally, while the single hospital network 20 is illustrated, the communication system may include one, two, three, four, ten, or more networks distributed through the hospital or other medical setting to provide desired coverage area for the communication system. The secondary transmitter 28, in some embodiments, communicates with the hospital network 20 via different access points 32' from the first transmitter 26 in a different band of radio frequency or through different wireless protocols. In another embodiment, the first 26 and second transmitter 28 communicate in the same band of frequency and wireless protocol but belong to different logical wireless networks.

As illustrated in FIG. 2, the PMD 12 transmits alarm signals 40 to the patient information server 22 and the mobile patient information display systems 24. In response to receiving the alarm signals 40 from a PMD 12, the patient information server 22 and the mobile patient information display systems 24 transmits an acknowledgement message 42, such as a ACK message, to the transmitting PMD 12 informing the PMD 12 that the alarm signal 40 was received by the patient information server 22 and the mobile patient information display systems 24.

In one embodiment, the first transmitter 26 of the PMD 12 transmits the alarm signal to the patient information server 22 and the mobile patient information display systems 24 through the hospital network 20 wirelessly using a primary channel. If the transmission of the alarm signal was successful, the communication 18 of the PMD 12 will receive an acknowledgement message and continue to process the patient's physiological data to determine whether the patient's condition warrants generating an alarm. If the PMD 12 does not receive an acknowledgement message 42 from transmission using the primary channel after a preselected number of attempts, the PMD 12 transmits the alarm signal in a subset of the second channel set concurrently with transmission of the alarm signal in the primary channel until an acknowledgement message has been received via one of the channels.

In another embodiment, the PMD 12 configures itself to use an automatic power-save delivery mode, such as IEEE 802.11 APSD protocol or the like. The first transmitter 26 of the PMD 12 transmits the alarm signal in the primary channel using IEEE 802.11 APSD protocol to the patient information server 22 and the mobile patient information display systems 24 through the hospital network 20 wirelessly for a predetermined amount of time or for a predetermined number of times. If the transmission of the alarm signal was successful, the PMD 12 will receive an acknowledgement message continues to process the patient's physiological data to determine whether the patient's condition warrants generating an alarm. If the PMD 12 does not receive an acknowledgement message 42 from transmission using the primary channel within the predetermined amount of time or the predetermined number of times, the PMD 12 will transmit the alarm signal in a subset of the secondary channel protocol for a predetermined amount of time or for a predetermined number of times while/concurrently using IEEE 802.11 APSD protocol in the primary channel. If the PMD 12 does not receive an acknowledgement message 42 from transmission using the secondary channel within the predetermined amount of time or for the predetermined number of times, the PMD 12 will return to transmitting the alarm signal in the primary channel using IEEE 802.11 APSD protocol for a predetermined amount of time or for a predetermined number of times. This will repeat until an acknowledgement message is received by the PMD 12.

It will be appreciated that each of the PMD 12, the WAP 32, the hospital IP network 20, the patient information server 22 and the mobile patient information display systems 24 described in various embodiments and figures herein include a memory or computer-readable medium (not shown) that stores, and one or more processors (not shown) that execute, computer-executable instructions for performing the various functions, actions, steps, methods, etc., described herein. The memory may be a computer-readable medium on which a control program is stored, such as a disk, hard drive, or the like. Common forms of computer-readable media include, for example, floppy disks, flexible disks, hard disks, magnetic tape, or any other magnetic storage medium, CD-ROM, DVD, or any other optical medium, RAM, ROM, PROM, EPROM, FLASH-EPROM, variants thereof, other memory chip or cartridge, or any other tangible medium from which the processor can read and execute. In this context, the systems described herein may be implemented on or as one or more general purpose computers, special purpose computer(s), a programmed microprocessor or microcontroller and peripheral integrated circuit elements, an ASIC or other integrated circuit, a digital signal processor, a hardwired electronic or logic circuit such as a discrete element circuit, a programmable logic device such as a PLD, PLA, FPGA, Graphical card CPU (GPU), or PAL, or the like.

With reference to FIG. 3, illustrated is a flowchart diagram of the operation of the PMD. In a step 100, a PMD connects with an access point in a primary channel using the preferred wireless technology of the primary channel, such as IEEE 802.11. The PMD collects physiological data from the associated patient and analyzes the data to determine if a condition warranting generation of alarm exists in a step 102. In a step 104, it is determined if an alarm condition is detected. If so, one or more attempts are made in the primary channel to transmit the alarm in a step 106. In step 106, the transmission of alarm(s) through primary channel is attempted at the maximum for a first pre-determined duration of time which is less than tolerable latency of the alarm transmission or a first pre-determined number of times. In a step 108, it is determined whether the alarm transmission was successful. If the alarm transmission has not been successful within the first pre-determined duration of time or after the first predetermined number of attempts, then one or more attempts are made to transmit the alarm in a subset of secondary channel set at the maximum for a second pre-determined duration or for a second predetermined number of times in a step 110. At the end of the second pre-determined duration or after second predetermined number of attempts, a check is made in the primary channel to detect if alarm transmission acknowledgement is received from the receiver in a step 112. Alternately, the step 110 can check for an acknowledgement message after each transmission from primary channel or one or more transmissions in the secondary channel. If a transmission reception acknowledgement is received then the PMD goes on to process physiological data to detect a further alarm condition in step 102. However, if the transmission reception acknowledgement is not received then the PMD continues to attempt to transmit the alarm one or more times in a subset of secondary channel set at the maximum for second pre-determined duration or for a second predetermined number of attempts in step 112.

With reference to FIG. 4, illustrated is a flowchart diagram of the operation of the PMD. In another embodiment, a PMD connects with an access point in a primary channel using the IEEE 802.11 wireless technology in the primary channel in a step 120. In a step 122, the PMD then configures itself to use IEEE 802.11 APSD protocol. In a step 124, the PMD collects physiological data from the associated patient and analyzes the data to determine if a condition warranting generation of alarm exists. In a step 126, it is determined whether an alarm condition is detected. If so, one or more attempts are made in the primary channel to transmit the alarm. The transmission of alarm(s) through primary channel is attempted at the maximum for a first predetermined duration of time which is less than tolerable latency of the alarm transmission or for a first predetermined number of times in a step 128. At the end of the first predetermined duration or after first predetermined number of transmission attempts, the PMD checks whether an acknowledgement to transmission reception is received in a step 130. In one embodiment, the PMD checks for an acknowledgement after each transmission attempt. If a transmission reception acknowledgement is received then the PMD goes on to process physiological data to detect alarm condition in step 124. However, if acknowledgement to transmission reception is not received, then one or more attempts are made to transmit the alarm in a subset of secondary channel set at the maximum for second pre-determined duration or for a second predetermined number of times in a step 132. At the end of second predetermined duration or after a second predetermined number of attempts, the PMD goes on to attempt to transmit the alarm in the primary channel one or more times in step 128. And the process repeats itself until an acknowledgement to transmission reception is received. The process could be terminated by a manual user intervention, such as resetting of the alarm condition.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A method for transmitting an alarm, comprising:
establishing a wireless communication link between a multi-mode patient monitoring device worn by a patient in a healthcare facility and at least one access point of a healthcare facility network which has a plurality of access points using an Internet protocol;
processing physiological data collected by the patient monitoring device to determine whether a patient's condition warrants generating an alarm;
attempting to transmit the alarm using a primary link between the patient monitoring device and the one or more access points for one of a first predetermined duration which is less than a preselected tolerable latency of the alarm transmission and a first number of attempts;
determining whether an acknowledgement message is received in response to the attempted transmissions;
if no acknowledgement message is received, repeating the attempting to transmit the alarm using the primary link for one of a first predetermined duration which is less than a preselected tolerable latency of the alarm transmission and a first number of attempts; and
transmitting the alarm using one or a subset of secondary links substantially concurrently with transmission using the primary link in response to the attempts to transmit the alarm using the primary link failing after the first predetermined period of time or the first predetermined number of attempts.

2. The method according to claim 1, wherein the alarm is transmitted on the secondary link after a preselected number of the attempts to transmit the alarm on the primary link without receiving the acknowledgment message.

3. A patient monitor, comprising:
a plurality of monitoring devices configured to collect data about a patient;
an evaluation unit configured to determine a patient's medical condition from the collected data and generate an alarm if the patient's condition warrants notifying an appropriate medical responder;
a first transmitter configured to transmit the alarm to one or more access points over a hospital Internet protocol (IP) network using a primary link with the Internet protocol (IP);
a second transmitter configured to transmit the alarm to the one or more access points using a secondary link in response to the transmission using the primary link failing; and,
a controller configured to:
control the first transmitter to repeatedly transmit the alarm for a maximum of a first predetermined duration that is less than an alarm latency duration or a predetermined number of attempts until an acknowledgment communication is received via the primary link,
in response to a failure to receive the acknowledgment communication after the preselected number of attempts or the first predetermined duration, control the secondary transmitter to transmit the alarm on a subset of secondary links for a second predetermined duration or a second predetermined number of attempts, and
monitor for receipt of the acknowledgment communication via the primary link responsive to a successful receipt of the alarm transmitted by one or both of the primary and secondary links.

4. The patient monitor according to claim 3, wherein the secondary link is at least one of a specific band of radio frequency, one or more links used for asset tracking tags, communication protocol(s) used for asset tracking tags in IEEE 802.11 networks, one or more links used for RFID tags, one or more links used for Bluetooth radios, and one or more links used for cellular networking technologies.

5. The patient monitor according to claim 3, wherein the patient monitor is a battery powered ambulatory patient worn monitor.

6. A patient monitoring system, comprising:
a plurality of patient monitors, each patient monitor including:
one or more monitoring devices configured to collect data about a patient;
a computer programmed to determine a patient's medical condition from the collected data and to generate an alarm if the patient's condition warrants notifying an appropriate medical responder; and
a communication system configured to transmit the alarm to one or more access points over a hospital Internet protocol (IP) network, wherein the communication system includes a first transmitter for transmitting the alarm using a primary link using the Internet protocol (IP) and a second transmitter for transmitting the alarm using a secondary link in response to the transmission using the primary link failing;
control the first transmitter to transmit the alarm;
if no acknowledgement message is received, controlling the first transmitter to repeatedly transmit the alarm;
if no acknowledgment message is received after a preselected duration or number of transmissions of the alarm by the first transmitter, controlling the second transmitter to transmit the alarm, on the subset of the secondary links, and
a patient information server in communication with the hospital IP network which displays and stores the transmitted alarm;
wherein the patient information server receives the alarm using a primary link with the Internet Protocol and upon failure of the primary link receives the alarm using a secondary link.

7. The patient monitoring system according to claim 6, wherein the secondary link is at least one of a specific band of radio frequency, one or more links used for asset tracking tags, communication protocol(s) used for asset tracking tags in IEEE 802.11 networks, one or more links used for RFID tags, one or more links used for Bluetooth radios, and one or more links used for cellular networking technologies.

8. The patient monitoring system according to claim 6, wherein the transmission of the alarm using the primary link is attempted at a maximum for a first pre-determined duration of time which is less than tolerable latency of the alarm transmission.

* * * * *